United States Patent [19]
Yamada

[11] Patent Number: 6,013,064
[45] Date of Patent: *Jan. 11, 2000

[54] MULTI-LAYER SANITARY NAPKIN

[75] Inventor: Ikuko Yamada, Tokyo, Japan

[73] Assignee: ASBE Co., Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 09/002,408

[22] Filed: Jan. 2, 1998

Related U.S. Application Data

[63] Continuation-in-part of application No. 08/842,574, Apr. 15, 1997, abandoned.

[30] Foreign Application Priority Data

Feb. 17, 1997 [JP] Japan ................................. 9-46928

[51] Int. Cl.[7] .................................................. A61F 13/15
[52] U.S. Cl. .................................. 604/385.1; 604/387
[58] Field of Search ............................ 604/385.1, 386, 604/387, 389, 358, 378, 344

[56] References Cited

U.S. PATENT DOCUMENTS

| | | | |
|---|---|---|---|
| 2,929,379 | 3/1960 | Poulsen | 604/372 |
| 2,964,039 | 12/1960 | Johnson | 604/385.1 |
| 3,575,174 | 4/1971 | Mogor | 604/385.1 |
| 4,023,571 | 5/1977 | Comerford et al. | 604/385.1 |
| 4,505,707 | 3/1985 | Feeney | 604/393 |
| 4,576,597 | 3/1986 | Hlaban | 604/389 |
| 4,685,914 | 8/1987 | Holtman | 604/385.1 |
| 4,894,058 | 1/1990 | Jensen | 604/344 |
| 5,074,856 | 12/1991 | Coe et al. | 604/370 |
| 5,429,631 | 7/1995 | Greiner | 604/393 |
| 5,599,339 | 2/1997 | Horney | 604/387 |
| 5,658,270 | 8/1997 | Lichstein | 604/387 |
| 5,688,259 | 11/1997 | Osborn et al. | 604/380 |
| 5,704,932 | 1/1998 | Hibbard | 604/385.1 |
| 5,720,738 | 2/1998 | Clark | 604/385.1 |

FOREIGN PATENT DOCUMENTS

| | | |
|---|---|---|
| 0 788 785 A1 | 6/1997 | European Pat. Off. . |
| 6121812 | 3/1994 | Japan ............................ 604/387 |
| WO 95/29655 | 11/1995 | WIPO . |

*Primary Examiner*—Mark O. Polutta
*Attorney, Agent, or Firm*—Armstrong, Westerman, Hattori, McLeland & Naughton

[57] ABSTRACT

A multi-layer sanitary napkin is provided which comprises a plurality of ordinary sanitary napkins for treating menses or leukorrhea in a single-use, each being provided with a waterproof sheet having a rim and an absorbing surface which is the top surface of an absorbing layer attached to the waterproof sheet, wherein the ordinary napkins are piled with respective absorbing surfaces thereof directed upward, and peelably joined with each other into unity at the rims by bonding, embossing or simultaneous bonding and embossing. Each of the ordinary napkins contained therein can be shaped as concave as a ship's bottom, to shape the entire figure of the multi-layer sanitary napkin in the same manner. The multi-layer sanitary napkin can further comprise pull tabs formed on either end of respective ordinary napkins, each tab being formed not so as to overlap on neighboring ones.

7 Claims, 1 Drawing Sheet

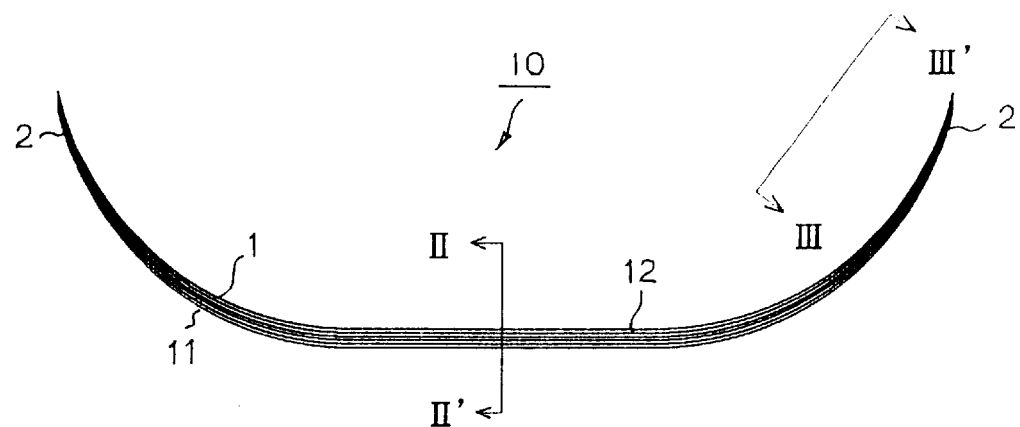
F I G. 1
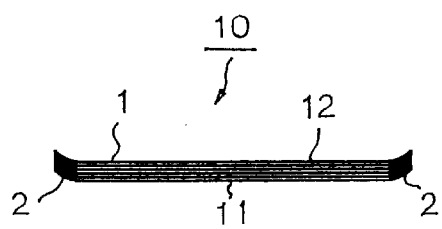
F I G. 2
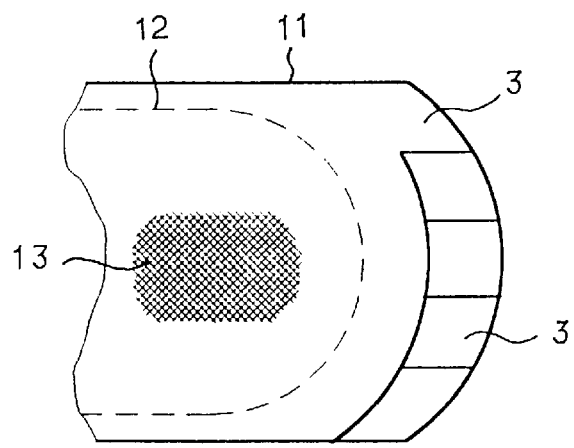
F I G. 3

MULTI-LAYER SANITARY NAPKIN

CROSS-REFERENCE TO RELATED APPLICATION

This application is a continuation in-part of U.S. application Ser. No. 08/842,574, filed Apr. 15, 1977 now abandoned.

BACKGROUND OF THE INVENTION

The field of art to which the invention pertains includes "bandage, covering articles or absorbing pads for physiological body-liquids such as urine or blood" as contained in IPC A61L 15/16.

STATE OF THE ART

Absorbing pads are used to treat woman's physiological discharges of menses or leukorrhea. Though the menses pad and leukorrhea pad are similarly structured, the latter is smaller than the former, having the length and width approximately half compared to those of the former. The former is used in a menses period, while the use of the latter is not restricted to a particular period, though the necessity thereof is different from person to person.

In the market, the menses pad and leukorrhea pad are often distinguished from each other by calling the former a "sanitary napkin" and the latter a "flows napkin", for instance. However, in this description, both are generally referred to as "sanitary napkins". Until now, sanitary napkins for menses or leukorrhea have been supplied only in a single-use form (hereinafter referred to as "ordinary napkins"). With an ordinary napkin, a woman is obliged to renew it frequently, and carry replacement napkins always with her in a pouch or something, which may cause her inconveniences and reservations of public notice.

The ordinary napkin typically comprises a waterproof sheet with a sticking agent applied to the back thereof, and an absorbing layer made of water-absorbent fibrous material attached to the waterproof sheet. The absorbing layer may be embossed to give unevenness on the surface thereof, or covered with a fine mesh screen.

The waterproof sheet avoids see page of moisture to the rear of the napkin, while the sticking agent sets the napkin onto the underwear surface to prevent it from slipping off. Menses blood or leukorrhea liquid is absorbed by the absorbing layer through the embossed surface thereof or the fine mesh screen covering the surface of the absorbing layer. The embossed surface or the fine mesh screen serves to improve the touch to the skin.

Recent advances in material science have enabled water-absorbent polymers to attain a very high absorption capability, which benefits the ordinary napkins in both aspects of enhancing the absorption capacity per napkin and lessening the thickness thereof. However, the direction of enhancing the absorption capacity is left within a certain level because of accompanying hygienic difficulties. Therefore, circumstances remain unchanged in which the ordinary napkin needs to be replaced with a new one before an absorption limit is reached.

SUMMARY OF THE INVENTION

The objective of the invention is to present another type of sanitary napkin for menses or leukorrhea which need not be carried explicitly for replacement, to lessen to some extent the aforementioned woman's mental burdens in relation to her physiological phenomena.

To attain the above objective, the present invention resides in a multi-layer sanitary napkin in which a plurality of ordinary napkins are piled with respective absorbing surfaces thereof directed upward and peelably joined with each other into unity at rims of the ordinary napkins.

In the above multi-layer sanitary napkin (hereinafter referred to as an "invented napkin"), 3 to 6 ordinary napkins for example, are piled and joined into unity. The idea of the invented napkin has arisen from the fact that today's ordinary napkins are so thin, less than 2 mm thick for example, that duplication or triplication of them in use can be done without any trouble.

One who wears the invented napkin can wear a bundle of ordinary napkins (hereinafter simply referred to as "pieces") for almost one day's consumption. When the uppermost piece approaches the absorption limit thereof, it is peeled off from the invented napkin and discarded, to expose the next absorbing surface for use.

To produce the invented napkin, it is necessary to join the pieces with each other in such a manner that each piece can be peeled off one after another. For joining the pieces in such manner, bonding the rims of the pieces together with a peelable bonding agent, embossing the rims of piled-up pieces between a pair of molds to produce a peelable mechanical connection between the rims, or simultaneously applying the are available.

It is preferable that respective absorbing surfaces of the pieces in the invented napkin are shaped as concave as a ship's bottom.

The preferable form of the invented napkin raised above can be realized by piling the pieces with the absorbing surfaces thereof pressed downward onto a mold having a convex surface, and joining the pieces together by bonding, embossing, or bonding and embossing simultaneously. Heat may also be applied at a temperature between a softening point and a melting point of the materials of the piece, specifically, those of the waterproof sheet.

Different from the above preferable form, if the pieces are piled and joined while the absorbing surfaces are kept flat, wrinkles can be formed on the top surface when the invented napkin is bent along the body's figure, which may cause a side leakage.

It is also preferable that the invented napkin is provided with pull tabs on either end of respective pieces, each tab being formed not so as to overlap on neighboring ones.

By pulling the pull tab raised above with fingers, the uppermost piece can easily be peeled off from the invented napkin. Each pull tab is formed not so as to overlap on neighboring ones, to make it easier than otherwise to hold the pull tab with fingers. The pull tabs are formed on either the front or rear end of respective pieces, because it is convenient to form the pull tabs in these spaces.

When a woman wears the invented napkin, she becomes free from carrying the replacement napkins and her mental burdens. since dirtied napkins are peeled off one after another and treated every few hours, cleanliness and good skin touch can be maintained.

BRIEF DESCRIPTION OF THE DRAWINGS

The present invention can be further understood by reference to the following description and attached drawings which illustrate a preferred embodiment.

In the drawings:

FIG. 1 shows a longitudinal cross-sectional view of a multi-layer sanitary napkin according to the embodiment;

FIG. 2 shows a lateral cross-sectional view of the multi-layer sanitary napkin seen in the direction of arrows II–II' drawn in FIG. 1; and FIG. 3 shows a partial plane view of the multi-layer sanitary napkin seen in the direction of arrows III–III' drawn in FIG. 1.

DESCRIPTION OF THE PREFERRED EMBODIMENT

FIGS. 1 and 2 in combination show the construction of a multi-layer sanitary napkin 10 according to a preferable embodiment of the invention, in which reference numeral 1 denotes an ordinary napkin constituting the multi-layer sanitary napkin 10, 11 a waterproof sheet, 12 an absorbing layer, 13 a fine mesh screen (see FIG. 3), 2 a junction layer formed on the rim of the multi-layer sanitary napkin 10, and 3 a pull tab formed on one end of each ordinary napkin 1, respectively.

As seen in FIGS. 1 and 2, the multi-layer sanitary napkin 10 comprises a plurality of the ordinary napkins 1 which are piled one on top of the other, with respective absorbing surfaces thereof directed upward, and peelably joined with each other into unity, at rims of the ordinary napkins 1. In the multi-layer sanitary napkin 10, respective absorbing surfaces of the ordinary napkins 1 are shaped as concave as a ship's bottom, so that the entire figure of the multi-layer sanitary napkin 10 is shaped in the same manner.

The multi-layer sanitary napkin 10 shaped concave in the above-mentioned manner is produced by applying a peelable bonding agent to the rim of each ordinary napkin 1, piling the ordinary napkins 1 with respective absorbing surfaces thereof directed downward on a mold having a convex surface like a ship's bottom, and embossing the rims of the piled-up ordinary napkins 1 with another mold while applying pressure and heat.

Since the multi-layer sanitary napkin 10 thus produced has been shaped in advance to fit the body's figure, breakdown wrinkles are hard to be formed on the top surface thereof when it is worn for use. A side leakage is effectively prevented and a good touch to the skin is given.

When the ordinary napkin 1 on top of the multi-layer sanitary napkin 10 approaches the absorption limit thereof, it can be peeled off to expose the next absorbing surface for use by pulling the pull tab 3 shown in FIG. 3.

What is claimed is:

1. A multi-layer sanitary napkin comprising a plurality of ordinary napkins for treating menses or leukorrhea in a single use, each ordinary napkin having an elongated shape with a rim provided around the same, and being provided with an absorbing surface and a waterproof layer, wherein respective said ordinary napkins are longitudinally and cross-sectionally concave on a side of the absorbing surface before use and piled on one another with respective absorbing surfaces thereof directed upward, and wherein each ordinary napkin is peelably joined with another napkin into unity at each of said rims.

2. A multi-layer sanitary napkin according to claim 1, wherein said rims are bonded with each other with a peelable bonding agent.

3. A multi-layer sanitary napkin according to claim 1, wherein said rims are embossed between a pair of molds to produce a peelable mechanical connection between said rims.

4. A multi-layer sanitary napkin according to claim 2, wherein said rims are further embossed between a pair of molds to produce a peelable mechanical connection between said rims.

5. A multi-layer sanitary napkin according to claim 3, wherein heat is applied during said embossing at a temperature between a softening point and a melting point of materials constituting said ordinary napkin.

6. A multi-layer sanitary napkin according to claim 4, wherein heat is applied during said embossing at a temperature between a softening point and a melting point of materials constituting said ordinary napkin.

7. A multi-layer sanitary napkin comprising a plurality of ordinary napkins for treating menses or leukorrhea in a single use, each ordinary napkin having an elongated shape with a rim provided around the same, and being provided with an absorbing surface and a waterproof layer, wherein respective said ordinary napkins are longitudinally and cross-sectionally concave on a side of the absorbing surface before use and piled on one another with respective absorbing surfaces thereof directed upward, and wherein each ordinary napkin is peelably joined with another napkin into unity at each of said rims, said multilayer sanitary napkin further comprising pull tabs formed on either end of respective said ordinary napkins, wherein each of said pull tabs is formed not so as to overlap neighboring ones.

* * * * *